United States Patent
Martinez et al.

(10) Patent No.: US 10,588,847 B2
(45) Date of Patent: Mar. 17, 2020

(54) COSMETIC COMPOSITION FOR TEMPORARILY SHAPING HAIR

(71) Applicant: Henkel AG & Co. KGaA, Duesseldorf (DE)

(72) Inventors: Cyrielle Martinez, Hamburg (DE); Maria Catalina Bermudez Agudelo, Darmstadt (DE); Julia Bibiane Lange, Bad Bramstedt (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/526,064

(22) PCT Filed: Oct. 2, 2015

(86) PCT No.: PCT/EP2015/072829
§ 371 (c)(1),
(2) Date: May 11, 2017

(87) PCT Pub. No.: WO2016/074852
PCT Pub. Date: May 19, 2016

(65) Prior Publication Data
US 2017/0319459 A1   Nov. 9, 2017

(30) Foreign Application Priority Data

Nov. 12, 2014  (DE) .................. 10 2014 223 088

(51) Int. Cl.
*A61K 8/81* (2006.01)
*A61K 8/86* (2006.01)
*A61K 9/19* (2006.01)
*A61Q 5/06* (2006.01)
*A61K 9/16* (2006.01)

(52) U.S. Cl.
CPC .......... *A61K 8/8176* (2013.01); *A61K 8/8152* (2013.01); *A61K 8/86* (2013.01); *A61K 9/1635* (2013.01); *A61Q 5/06* (2013.01); *A61K 2800/594* (2013.01)

(58) Field of Classification Search
CPC ............ A61K 2800/594; A61K 8/8152; A61K 8/8176; A61K 8/86; A61K 9/1635; A61Q 5/06
See application file for complete search history.

(56) References Cited

U.S. PATENT DOCUMENTS

| | | |
|---|---|---|
| 6,190,647 B1 | 2/2001 | Karlen et al. |
| 2012/0064023 A1 | 3/2012 | Knappe et al. |
| 2014/0093467 A1* | 4/2014 | Knappe ................ A61K 8/8152 424/70.15 |
| 2014/0305462 A1 | 10/2014 | Knappe et al. |
| 2015/0150777 A1 | 6/2015 | Knappe et al. |
| 2015/0335566 A1 | 11/2015 | Knappe et al. |

FOREIGN PATENT DOCUMENTS

| | | | |
|---|---|---|---|
| DE | 102011077364 | * 12/2012 | |
| DE | 102013225753 | * 5/2014 | ............... A61K 8/73 |
| DE | 102013225753 A1 | 5/2014 | |

OTHER PUBLICATIONS (EWG's Skin Deep Cosmetic Database: Carbomer, 2017 https://www.ewg.org/skindeep/ingredient/701088/CARBOMER/) (Year: 2017).*
To AzkoNoble (Balance RCF Polymer, http://www.bannerquimica.com/hcare/hcare-tecnica/ESPESANTES/TDS%20 BALANCE%20RCF%20POLYMER.pdf Sep. 3, 2014), (Year: 2014).*
EPO, International Search Report and Written Opinion issued in International Application No. PCT/EP2015/072829, dated Dec. 17, 2015.

* cited by examiner

*Primary Examiner* — Anna R Falkowitz
(74) *Attorney, Agent, or Firm* — Lorenz & Kopf, LLP

(57) ABSTRACT

A cosmetic composition and a method temporarily shaping keratinic fiber including the same are provided herein. In one embodiment, the cosmetic composition includes at least one vinylpyrrolidone homopolymer. The cosmetic composition further includes at least one crosslinked acrylate copolymer. In another embodiment, the method includes providing a cosmetic composition. The method further includes applying the cosmetic composition to keratinic fiber.

12 Claims, No Drawings

COSMETIC COMPOSITION FOR TEMPORARILY SHAPING HAIR

CROSS-REFERENCE TO RELATED APPLICATION

This application is a U.S. National-Stage entry under 35 U.S.C. § 371 based on International Application No. PCT/EP2015/072829, filed Oct. 2, 2015, which was published under PCT Article 21(2) and which claims priority to German Application No. 10 2014 223 088.8, filed Nov. 12, 2014, which are all hereby incorporated in their entirety by reference.

TECHNICAL FIELD

The present disclosure relates to a cosmetic composition for setting hair or for temporarily shaping keratinic fibers, in particular human hair, the composition containing a combination of a specific acrylate copolymer and a vinylpyrrolidone homopolymer.

BACKGROUND

The temporary shaping of hairstyles for an extended period of up to several days generally requires the use of setting active ingredients. Hair treatment agents that are used for temporarily shaping the hair therefore play an important role. Such agents for temporary shaping typically contain synthetic polymers and/or waxes as the setting active ingredient. Agents for assisting with the temporary shaping of keratin-containing fibers may be provided as a hair spray, hair wax, hair gel, or hair foam, for example.

The most important property of an agent for temporarily shaping hair, also referred to below as a styling agent, is to provide the strongest hold possible for the treated fibers in the reshaped form, i.e., a shape that is imparted to the hair. This is also referred to as a strong hairstyle hold, or a high degree of hold of the styling agent. The hold of the hairstyle is determined essentially by the type and quantity of the setting active ingredients used, although there may also be an influence by the other components of the styling agent.

Styling agents must meet a number of requirements in addition to a high degree of hold. These requirements may be roughly divided into properties on the hair, properties of the particular formulation, for example properties of the foam, gel, or sprayed aerosol, and properties that affect the handling of the styling agent, with particular importance being accorded to the properties on the hair. These include moisture resistance, low tack, and a balanced conditioning effect in particular. In addition, a styling agent should preferably be universally usable for all types of hair, and be mild on the hair and skin.

In order to meet the various requirements, a number of synthetic polymers as setting active ingredients have already been developed for use in styling agents. The polymers may be divided into cationic, anionic, nonionic, and amphoteric setting polymers. Ideally, when applied to the hair the polymers result in a polymer film which on the one hand imparts a strong hold to the hairstyle, but on the other hand is sufficiently flexible not to break down under stress. If the polymer film is too brittle, this results in so-called film plaques, i.e., residues that come off when the hair moves and give the impression that the user of the styling agent in question has dandruff. Similar problems arise when waxes are used as a setting active ingredient in the styling agent. If the styling agent is a gel or a paste, the polymers should also have thickening properties.

BRIEF SUMMARY

A cosmetic composition and a method temporarily shaping keratinic fiber including the same are provided herein. In one embodiment, the cosmetic composition includes at least one vinylpyrrolidone homopolymer. The cosmetic composition further includes at least one crosslinked acrylate copolymer including at least of the following structural units (b-1) and (b-2),

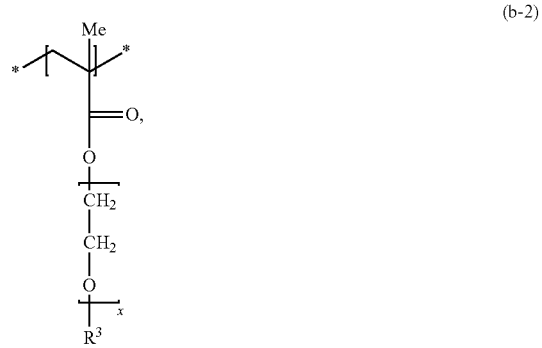

where $R^1$ stands for a hydrogen atom or a methyl group, $R^3$ stands for a $(C_8\text{-}C_{30})$ alkyl group, $M^+$ stands for a physiologically acceptable cation, and x stands for an integer from 5 to 35.

In another embodiment, the method includes providing a cosmetic composition. The cosmetic composition includes at least one vinylpyrrolidone homopolymer. The cosmetic composition further includes at least one crosslinked acrylate copolymer including at least of the following structural units (b-1) and (b-2),

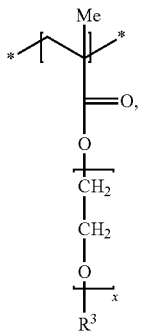

(b-2)

where R¹ stands for a hydrogen atom or a methyl group, R³ stands for a (C₈-C₃₀) alkyl group, M⁺ stands for a physiologically acceptable cation, and x stands for an integer from 5 to 35. The method further includes applying the cosmetic composition to keratinic fiber.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Crosslinked anionic amphiphilic polymers containing a (meth)acrylic acid unit and a (meth)acrylic acid oxyalkylene alkyl ester unit are known anionic polymers that are used in hair setting products. Such polymers are described in EP 897711 B1, DE 102011077364 A1, and DE 102009001978 A1, for example, and are commercially available under the name Aculyn® 88 (INCI: Acrylates/Steareth-20 Methacrylate Crosspolymer). DE 10 2011 077 364 A1 and DE 10 2009 001 978 A1 relate to the use of such a polymer, in particular Aculyn® 88, in combination with a further specific crosslinked anionic polymer, for temporarily shaping hair.

A similar polymer is commercially available under the name BALANCE® RTF (INCI: Acrylates/Ceteareth-20 Methacrylate Crosspolymer), whose function in styling products is essentially that of a thickener and film-forming agent.

Polyvinylpyrrolidones (PVP) are known nonionic polymers that are used in hair setting products. Polyvinylpyrrolidones are homopolymers of vinylpyrrolidone. Vinylpyrrolidone homopolymers are marketed under the name Luviskol® (BASF), for example, and are typically used as film-forming agents and/or thickeners. The Luviskol® K product line (BASF), which provides vinylpyrrolidone homopolymers in various molecular weights, is available in particular for use in cosmetic compositions and styling products as a film-forming agent or thickener.

It is an object of the present disclosure to provide further suitable polymer combinations that are characterized by good film-forming and/or setting properties and a very high degree of hold without having to sacrifice flexibility and good moisture resistance, in particular resistance to perspiration and water, and which also are suitable for producing stable viscous as well as stable transparent cosmetic compositions. In particular, currently available styling agents may be even further improved for a desired better combination of stiffness and long-term hold. It is therefore an object of the present disclosure to provide such styling agents which, in addition to the properties mentioned above, in particular result in an excellent combination of the properties stiffness and long-term hold.

These objects are achieved as contemplated herein by a combination of a specific crosslinked anionic acrylate resin and a specific nonionic polymer.

The present disclosure provides the following:

1. A cosmetic composition for temporarily shaping keratinic fibers, containing:
   (a) at least one vinylpyrrolidone homopolymer and
   (b) at least one crosslinked acrylate copolymer composed at least of the following structural units (b-1) and (b-2):

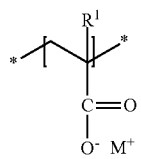

(b-1)

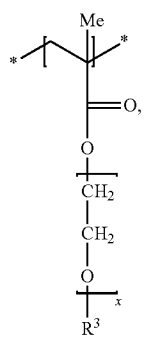

(b-2)

where
R¹ stands for a hydrogen atom or a methyl group,
R³ stands for a (C₈-C₃₀) alkyl group,
M⁺ stands for a physiologically acceptable cation, and
x stands for an integer from 5 to 35, in particular an integer from 10 to 24.

2. The cosmetic composition according to item 1, wherein the vinylpyrrolidone homopolymer (a) has a K value in water of about 20 to 100 (1% by weight solution of PVP, Brookfield, at 23° C.).

3. The cosmetic composition according to item 1 or 2, wherein the vinylpyrrolidone homopolymer (a) has a K value of about 80 to 100, in particular approximately 90.

4. The cosmetic composition according to one of the preceding items, wherein x in the crosslinked acrylate copolymer (b) stands for the integer 20, and R³ stands for a C16 and/or C18 alkyl group, in particular a combination of stearyl and cetyl groups.

5. The cosmetic composition according to one of the preceding items, wherein a crosslinked acrylate copolymer with the INCI name Acrylates/Ceteareth-20 Methacrylate Crosspolymer, preferably BALANCE® RCF, is contained as the crosslinked acrylate copolymer (b).

6. The cosmetic composition according to one of the preceding items, wherein the composition also contains at least one thickener, in particular a carbomer.

7. The cosmetic composition according to one of the preceding items, wherein the vinylpyrrolidone homopolymer (a) has a K value of about 80 to 100, in particular approximately 90, and the crosslinked acrylate copolymer (b) has the INCI name Acrylates/Ceteareth-20 Methacrylate Crosspolymer.

8. The cosmetic composition according to one of the preceding items, which, based on the total weight of the cosmetic composition, contains:
about 0.01 to about 3.0% by weight of the vinylpyrrolidone homopolymer (a) and
about 0.01 to about 2.0% by weight of the acrylate copolymer (b).

9. The cosmetic composition according to one of the preceding items, which, based on the total weight of the cosmetic composition, contains:
about 0.2 to about 2.0% by weight of the vinylpyrrolidone homopolymer (a) and
about 0.1 to about 1.2% by weight of the acrylate copolymer (b).

10. The cosmetic composition according to one of items 6 to 9, which, based on the total weight of the cosmetic composition, contains:
about 0.05 to about 1.5% by weight of the carbomer.

11. The cosmetic composition according to one of the preceding items, wherein the composition is present as a hair gel, hair spray, hair wax, or hair foam.

12. Use of a cosmetic composition according to one of items 1 to 11 for temporarily shaping keratinic fibers.

13. A method for temporarily shaping keratinic fibers, in particular human hair, in which the cosmetic composition according to one of items 1 to 11 is applied to keratinic fibers.

Within the scope of the present disclosure, it was surprisingly found that a greatly improved combination of long-term effect and stiffness of styling products, in particular hair gels, may be obtained by combining two polymers known per se, wherein the two required components appear to interact synergistically. Such a combination of good stiffness and good long-term hold was not expected.

As contemplated herein, the term "keratinic fibers" comprises fur, wool, and feathers, but in particular human hair.

The essential components of the cosmetic composition as contemplated herein are the vinylpyrrolidone homopolymer (a) and the crosslinked acrylate copolymer (b).

The agent as contemplated herein must contain a vinylpyrrolidone homopolymer as component (a). As contemplated herein, it is preferred to select the vinylpyrrolidone homopolymers from vinylpyrrolidone homopolymers having a K value in water of about 20 to 100 (1% by weight solution of PVP, Brookfield, at 23° C.). A K value of about 80 to 100 is more preferable, and a K value of approximately 90 is even more preferable. The K value, also referred to as the intrinsic viscosity, is a parameter for characterizing polymers, and is easily determinable from the relative viscosity by employing viscosity measurements of polymer solutions.

Preferred vinylpyrrolidone homopolymers are available under the trade names Luviskol® K 30, Luviskol® K 80, Luviskol® K 85, and Luviskol® K 90 from BASF SE. Luviskol® K 90 is most preferred as contemplated herein. Luviskol® K90 is a 20% aqueous, colorless to light yellowish solution of polyvinylpyrrolidone. The product has a K value of about 90.0 to about 98.0 (1% (m/V) in water), a solids content of about 19.0 to about 21.0% by weight, and a pH of about 7.0 to about 9.0 (10% by weight solids content in water).

The crosslinked anionic acrylate copolymer (b) is composed at least of the following structural units (b-1) and (b-2):

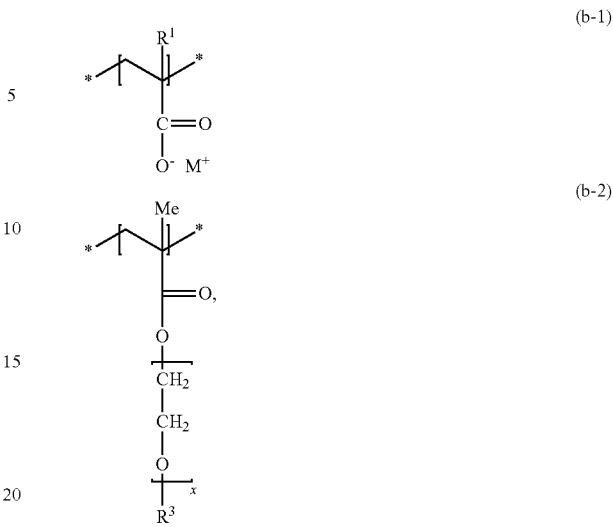

where
$R^1$ stands for a hydrogen atom or a methyl group,
$R^3$ stands for a ($C_8$-$C_{30}$) alkyl group,
$M^+$ stands for a physiologically acceptable cation, and
x stands for an integer from 5 to 35, in particular an integer from 10 to 24.

The crosslinked acrylate copolymer (b) is amphiphilic due to the structural units that it contains. Those skilled in the art generally understand "amphiphilic" to mean that the same molecule includes hydrophilic structural elements (for example, those of formula (b-1)) and lipophilic structural elements (for example, those of formula (b-2)).

In the above formulas and all of the following formulas, a chemical bond denoted by the symbol "*" stands for a free valence of the structural fragment in question. Metal cations of the physiologically acceptable metals from groups Ia, Ib, IIa, IIb, IIIb, VIa, or VIII of the periodic table of the elements, ammonium ions, and cationic organic compounds having a quaternized nitrogen atom are particularly suited as physiologically acceptable cations M+ for compensating for the negative charge of the amphiphilic, anionic polymers. Cationic organic compounds having a quaternized nitrogen atom are formed, for example, by protonation of primary, secondary, or tertiary organic amines with an acid, or by permanent quaternization of these organic amines. Examples of these cationic organic ammonium compounds are 2-ammonium ethanol and 2-trimethylammonium ethanol.

Within the meaning of the invention, "crosslinked" or "crosslinking" is the linkage of polymer chains to one another by covalent chemical bonding to form a network. This covalent linkage of the polymer chains may take place by direct covalent bonding, or may be provided by a molecular fragment that bridges the polymer chains. The molecular fragment bonds to the polymer chains bridged by the molecular fragment by employing covalent chemical bonding in each case.

The crosslinking of the crosslinked, amphiphilic, anionic polymers (b) may preferably be brought about by using at least one crosslinked monomer. It is in turn preferable to select the crosslinked monomers from at least one compound of the group comprising polyunsaturated aromatic monomers (for example, divinylbenzene, divinylnaphthalene, trivinylbenzene), polyunsaturated alicyclic monomers (for example, 1,2,4-trivinylcyclohexane), difunctional esters of phthalic acid (for example, diallyl phthalate), polyunsaturated aliphatic monomers (for example, dienes, trienes, or tetraenes such as isoprene, 1,3-butadiene, 1,5-hexadiene, 1,5,9-decatriene, 1,9-decadiene, 1,5-heptadiene), polyalkenyl ethers (for example, triallyl pentaerythritol, diallyl pentaerythritol, diallyl sucrose, octaallyl sucrose, trimethylolpropane diallyl ether), polyunsaturated esters of polyalcohols or polyacids (for example, 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, polyethylene glycol di(meth)acrylate), alkylene bisacrylamides (for example, methylene bisacrylamide, propylene bisacrylamide), hydroxy and carboxy derivatives of methylene bisacrylamide (for example, N,N'-bismethylol methylene bisacrylamide), polyethylene glycol di(meth)acrylates (for example, ethylene glycol di(meth)acrylate, diethylene glycol di(meth)acrylate, triethylene glycol di(meth)acrylate), polyunsaturated silanes (for example, dimethyldivinylsilane, methyltrivinylsilane, allyldimethylvinylsilane, diallyldimethylsilane, tetravinylsilane), N-methylol acrylamide; N-alkoxy(meth)acrylamide, where the alkoxy group is a (C1 to C18) alkoxy group, unsaturated hydrolyzable silanes (for example, triethoxyvinylsilane, trisisopropoxyvinylsilane, 3-triethoxysilylpropyl methacrylate), hydrolyzable silanes (for example, ethyltriethoxysilane, ethyltrimethoxysilane), epoxy-substituted hydrolyzable silanes (for example, 2-(3,4-epoxycyclohexyl)ethyltriethoxysilane, 3-glycidoxypropyltrimethyoxysilane), polyisocyanates (for example, 1,4-diisocyanatobutane, 1,6-diisocyanatohexane, 1,4-phenylene diisocyanate, 4,4'-oxybis(phenyl isocyanate), unsaturated epoxides (for example, glycidyl methacrylate, allyl glycidyl ether), polyepoxides (for example, diglycidyl ether, 1,2,5,6-diepoxyhexane, ethylene glycol diglycidyl ether), ethoxylated polyols (for example, diols, triols, and diphenols), in each case ethoxylated with 2 to 100 moles of ethylene oxide per mole of hydroxyl groups and terminated with a polymerizable unsaturated group, for example vinyl ether, allyl ether, acrylate ester, methacrylate ester; examples include bisphenol A ethoxylated di(meth)acrylate, bisphenol F ethoxylated di(meth)acrylate, ethoxylated trimethylolpropane tri(meth)acrylate, acrylate and methacrylate esters of polyols having at least two acrylate ester or methacrylate ester functionalities (for example, trimethylolpropane triacrylate (TMPTA), trimethylolpropane ethoxylated (15) triacrylate (TMPEO15TA), trimethylolpropane dimethacrylate, triethylene glycol dimethacrylate (TEGDMA), and bisphenol A dimethacrylate ethoxylated with 30 moles of ethylene oxide (EOBDMA)).

As contemplated herein, copolymer (b) may be composed of further structural units. According to embodiments of the invention, however, copolymer (b) is composed only of units (b-1) and (b-2); i.e., it consists of these structural units.

The at least one unit (b-1) is a (meth)acrylic acid unit, and as contemplated herein may be a methacrylic acid unit and/or acrylic acid unit.

x in unit (b-2) of the crosslinked acrylate copolymer (b) preferably stands for an integer from 10 to 24, more preferably 16 to 22, most preferably 20.

R3 in unit (b-2) of the crosslinked acrylate copolymer (b) preferably stands for a (C12-C20) alkyl group, more preferably a (C14-C20) alkyl group, likewise preferably a (C16-C18) alkyl group. The alkyl group is preferably linear, but may also be branched. R3 is more preferably a combination of linear C16 and C18 alkyl groups, i.e., stearyl and cetyl groups (INCI name: Ceteareth).

A crosslinked acrylate copolymer having the INCI name Acrylates/Ceteareth-20 Methacrylate Crosspolymer is most preferably contained as crosslinked acrylate copolymer (b). The crosslinked acrylate copolymer available under the trade name BALANCE® RCF (AkzoNobel) is very particularly preferred as the crosslinked acrylate copolymer (b). This product is an approximately 30% by weight dispersion in water.

In one particularly preferred embodiment of the present disclosure, the cosmetic composition contains the copolymer commercially available under the name Luviskol® K90 (BASF) as the vinylpyrrolidone homopolymer (a), and contains the copolymer commercially available under the name BALANCE® RCF as the anionic crosslinked acrylate copolymer (b). With this combination, particularly good results have been achieved with regard to a combination of stiffness and long-term hold in various packagings.

Further properties of styling products that are generally required, such as moisture resistance and low tack, are likewise achieved in particular with this combination.

The cosmetic composition of the present disclosure contains the vinylpyrrolidone homopolymer (a) and the acrylate copolymer (b) in quantities that are customary and suitable for styling agents, and which may be adapted to the specific application and type of packaging.

The cosmetic composition as contemplated herein contains the vinylpyrrolidone homopolymer (a), based on the total weight of the cosmetic composition, for example in a quantity of about 0.01 to about 5.0% by weight, preferably about 0.1 to about 3.0% by weight, more preferably about 0.2 to about 2.0% by weight, even more preferably about 0.5 to about 1.5% by weight or about 0.8 to about 1.2% by weight, in each case expressed as the solids content of active substance in the cosmetic composition.

The cosmetic composition as contemplated herein contains the crosslinked acrylate copolymer (b), based on the total weight of the cosmetic composition, for example in a quantity of about 0.01 to about 3.0% by weight, preferably about 0.015 to about 1.5% by weight, more preferably about 0.1 to about 1.2% by weight, preferably about 0.5 to about 1.5% by weight or about 0.8 to about 1.2% by weight, even more preferably about 0.2 to about 0.7% by weight, in each case expressed as the solids content of active substance in the cosmetic composition.

The cosmetic composition of the present disclosure preferably contains one or more further component(s) which act(s) as a thickener or gel-forming agent and which is/are different from the vinylpyrrolidone homopolymer (a) and the crosslinked acrylate copolymer (b), and likewise assist(s) with film formation. Examples are cationic, anionic, nonionic. or amphoteric polymers. The weight fraction of this/these further component(s) in the total weight of the cosmetic composition may be comparatively low due to the presence of components (a) and (b), and for example is about 0.02 to about 3% by weight, preferably about 0.05 to about 1.5% by weight, more preferably about 0.2 to about 0.8% by weight.

However, the present disclosure also encompasses embodiments in which the cosmetic composition contains no other components besides components (a) and (b) that act as thickeners, film-forming agents, or gel-forming agents.

Examples are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/OctylacrylamideCopolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/lsophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, *Bacillus*/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Poly-beta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-55, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/lsophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VPNA Copolymer, VP/Vinyl Caprolactam/DMAPA Acrylates Copolymer, Yeast Palmitate, and Styrene NP Copolymer.

The following are examples of nonionic polymers:

vinylpyrrolidone/vinyl ester copolymers, as marketed under the trademark Luviskol (BASF), for example. Luviskol VA 64 and Luviskol VA 73, which are vinylpyrrolidone/vinyl acetate copolymers, are preferred nonionic polymers.

cellulose ethers such as hydroxypropyl cellulose, hydroxyethyl cellulose, and methylhydroxypropyl cellulose, as marketed under the trademarks Culminal and Benecel (Aqualon), for example.

shellac.

siloxanes. These siloxanes may be water-soluble or also water-insoluble. Volatile as well as nonvolatile siloxanes are suitable; nonvolatile siloxanes are understood to mean those compounds having a boiling point above 200° C. at standard pressure. Preferred siloxanes are polydialkylsiloxanes such as polydimethylsiloxane, polyalkylarylsiloxanes such as polyphenylmethylsiloxane, ethoxylated polydialkylsiloxanes, and polydialkylsiloxanes containing amine and/or hydroxy groups.

glycosidically substituted silicones.

The further component, which acts as a gel-forming agent, is preferably a homopolyacrylic acid (INCI: Carbomer), commercially available in various versions under the name Carbopol®. The carbomer is preferably contained in a proportion of about 0.02 to about 3% by weight, more preferably about 0.05 to about 1.5% by weight, and even more preferably about 0.2 to about 0.8% by weight, based on the total weight of the cosmetic composition. In embodiments of the invention, the cosmetic composition contains no other components besides components (a) and (b) and the carbomer as components that act as gel-forming agents, film-forming agents, or thickeners.

The cosmetic composition as contemplated herein may contain further substances that are customary in styling products. In particular, additional care substances are mentioned as further suitable auxiliary materials and additives.

The agent may contain, for example, at least one protein hydrolysate and/or one of the derivatives thereof as care substance. Protein hydrolysates are product mixtures that are obtained by acidically, basically, or enzymatically catalyzed degradation of proteins. As contemplated herein, the "protein hydrolysates" is also understood to mean total hydrolysates as well as individual amino acids and the derivatives thereof, in addition to mixtures of various amino acids. The molecular weight of the protein hydrolysates usable as contemplated herein is between about 75 Dalton, the molecular weight of glycine, and about 200,000 Dalton; the molecular weight is preferably about 75 to about 50,000 Dalton, and very particularly preferably about 75 to about 20,000 Dalton.

The agent as contemplated herein may also contain at least one vitamin, one provitamin, one vitamin precursor, and/or one of the derivatives thereof as care substance. Vitamins, provitamins, and vitamin precursors customarily associated with the groups A, B, C, E, F, and H are preferred as contemplated herein.

The addition of panthenol as well as glycerin and/or propylene glycol increases the flexibility of the polymer film that is formed during use of the agent as contemplated herein.

The agents as contemplated herein may also contain at least one plant extract, or also mono- or oligosaccharides and/or lipids, as care substance.

Oil bodies are also suitable as care substances. The natural and synthetic cosmetic oil bodies include, for example, plant oils, liquid paraffin oils, isoparaffin oils, and synthetic hydrocarbons, as well as di-n-alkyl ethers having a total of 12 to 36 C atoms, in particular 12 to 24 C atoms. Preferred cosmetic agents as contemplated herein contain at least one oil body, preferably at least one oil body from the group of silicone oils. The group of silicone oils includes in particular dimethicones, which also include cyclomethicones, aminofunctional silicones, and dimethiconols. The dimethicones may be linear or branched, as well as cyclic or cyclic and branched. Suitable silicone oils or silicone gums are in particular dialkyl and alkylaryl siloxanes, for example dimethylpolysiloxane and methylphenylpolysiloxane, and the alkoxylated, quaternized, or anionic derivatives thereof. Cyclic and linear polydialkylsiloxanes, the alkoxylated and/or aminated derivatives thereof, dihydroxypolydimethylsiloxanes, and polyphenylalkylsiloxanes are preferred.

Further preferred oil bodies as care substances are ester oils, i.e., esters of C6-C30 fatty acids with C2-C30 fatty alcohols, preferably monoesters of the fatty acids with alcohols containing 2 to 24 C atoms, for example isopropyl myristate (Rilanit® IPM), isononanoic acid-C16-18 alkyl ester (Cetiol® SN), 2-ethylhexyl palmitate (Cegesoft® 24), stearic acid-2-ethylhexyl ester (Cetiol® 868), cetyl oleate, glycerin tricaprylate, coco fatty alcohol-caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V).

Also suitable as care substances are dicarboxylic acid esters, symmetrical, asymmetrical, or cyclic esters of carbonic acid with fatty alcohols, and trifatty acid esters of saturated and/or unsaturated linear and/or branched fatty acids with glycerin or fatty acid partial glycerides, which are understood to include monoglycerides, diglycerides, and the technical mixtures thereof.

In addition, emulsifiers or surface-active agents are preferably contained in the composition as contemplated herein. PEG derivatives of hydrogenated castor oil, which are available, for example, under the name PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil, or PEG-40 Hydrogenated Castor Oil, are preferred. The use of PEG-40 Hydrogenated Castor Oil is preferred as contemplated herein, and is preferably contained in a quantity of about 0.05 to about 1.5% by weight, preferably about 0.1 to about 1.0% by weight, likewise preferably about 0.2 to about 0.8% by weight, or about 0.3 to about 0.6% by weight.

The cosmetic composition of the present disclosure may also contain neutralizers or pH adjusters for setting the pH. Primary amino alcohols are examples of neutralizers used in styling products. One example of such a neutralizer that is preferably usable as contemplated herein is Aminomethyl Propanol (INCI), commercially available under the name AMP Ultra® PC, for example. AMP Ultra® PC 2000, containing 5% water, is preferred as contemplated herein.

The cosmetic agents as contemplated herein contain the ingredients and active substances in a cosmetically acceptable carrier.

Preferred cosmetically acceptable carriers are aqueous, alcoholic, or aqueous-alcoholic media preferably containing at least about 10% by weight water, calculated based on the total weight of the agent.

The cosmetic carrier as contemplated herein particularly preferably contains water, in particular in the quantity that the cosmetic agent contains at least about 10% by weight, in particular at least about 20.0% by weight, most preferably at least about 40% by weight, water, calculated based on the total weight of the agent.

In particular the lower alcohols having 1 to 4 carbon atoms which are typically used for cosmetic purposes, for example ethanol and isopropanol, may be contained as alcohols.

Examples of water-soluble solvents as cosolvents are glycerin and/or ethylene glycol and/or 1,2-propylene glycol in a quantity of 0 to about 30% by weight, based on the overall agent.

The cosmetic composition of the present disclosure may be provided in forms that are customary for the temporary shaping of hair, for example as a hair gel, hair spray, hair foam, or hair wax. Provision as a hair gel is preferred.

Hair foams as well as hair sprays require the presence of propellants. As contemplated herein, the propellants customarily employed in cosmetic agents are usable. Dimethyl ether is a suitable propellant as contemplated herein.

The present disclosure further relates to the use of cosmetic compositions as contemplated herein for temporarily shaping keratinic fibers, in particular human hair, and to a method for temporarily shaping keratinic fibers, in particular human hair, in which the cosmetic composition as contemplated herein is applied to keratinic fibers.

Overview in Tabular Form

The compositions of several preferred cosmetic agents are provided in the following tables (unless stated otherwise, entries are in % by weight, based on the total weight of the cosmetic agent).

|  | Formula 1 | Formula 2 | Formula 3 | Formula 4 | Formula 5 |
|---|---|---|---|---|---|
| Vinylpyrrolidone homopolymer (a) | 0.05 to 3.0 | 0.1 to 2.5 | 0.2 to 2.0 | 0.5 to 1.5 | 0.8 to 1.2 |

-continued

|  | Formula 1 | Formula 2 | Formula 3 | Formula 4 | Formula 5 |
| --- | --- | --- | --- | --- | --- |
| Copolymer (b) | 0.01 to 5.0 | 0.15 to 4.0 | 0.1 to 2.0 | 0.5 to 1.5 | 0.2 to 0.7 |
| Miscellaneous | To make 100 | To make 100 | To make 100 | To make 100 | To make 100 |

|  | Formula 1a | Formula 2a | Formula 3a | Formula 4a | Formula 5a |
| --- | --- | --- | --- | --- | --- |
| Vinylpyrrolidone homopolymer (a) having a K value of 80 to 100 (expressed as solids content) | 0.05 to 3.0 | 0.1 to 2.5 | 0.2 to 2.0 | 0.5 to 1.5 | 0.8 to 1.2 |
| Copolymer (b): Acrylates/Ceteareth-20 Methacrylate Crosspolymer | 0.01 to 5.0 | 0.15 to 4.0 | 0.1 to 2.0 | 0.5 to 1.5 | 0.2 to 0.7 |
| Miscellaneous | To make 100 | To make 100 | To make 100 | To make 100 | To make 100 |

|  | Formula 1b | Formula 2b | Formula 3b | Formula 4b | Formula 5b |
| --- | --- | --- | --- | --- | --- |
| Vinylpyrrolidone homopolymer (a): Luviskol ® K 90 - 20% (expressed as solids content) | 0.05 to 3.0 | 0.1 to 2.5 | 0.2 to 2.0 | 0.5 to 1.5 | 0.8 to 1.2 |
| Copolymer (b): BALANCE ® RCF (expressed as solids content) | 0.01 to 5.0 | 0.15 to 4.0 | 0.1 to 2.0 | 0.5 to 1.5 | 0.2 to 0.7 |
| Miscellaneous | To make 100 | To make 100 | To make 100 | To make 100 | To make 100 |

|  | Formula 11 | Formula 12 | Formula 13 | Formula 14 | Formula 15 |
| --- | --- | --- | --- | --- | --- |
| Vinylpyrrolidone homopolymer (a) | 0.05 to 3.0 | 0.1 to 2.5 | 0.2 to 2.0 | 0.5 to 1.5 | 0.8 to 1.2 |
| Copolymer (b) | 0.01 to 5.0 | 0.15 to 4.0 | 0.1 to 2.0 | 0.5 to 1.5 | 0.2 to 0.7 |
| Carbomer | 0.02 to 3.0 | 0.05 to 2.0 | 0.05 to 1.5 | 0.2 to 1.0 | 0.35 to 0.8 |
| Miscellaneous | To make 100 | To make 100 | To make 100 | To make 100 | To make 100 |

|  | Formula 11a | Formula 12a | Formula 13a | Formula 14a | Formula 15a |
| --- | --- | --- | --- | --- | --- |
| Vinylpyrrolidone homopolymer (a) having a K value of 80 to 100 (expressed as solids content) | 0.05 to 3.0 | 0.1 to 2.5 | 0.2 to 2.0 | 0.5 to 1.5 | 0.8 to 1.2 |
| Copolymer (b): Acrylates/Ceteareth-20 Methacrylate Crosspolymer | 0.01 to 5.0 | 0.15 to 4.0 | 0.1 to 2.0 | 0.5 to 1.5 | 0.2 to 0.7 |
| Carbomer | 0.02 to 3.0 | 0.05 to 2.0 | 0.05 to 1.5 | 0.2 to 1.0 | 0.35 to 0.8 |
| Miscellaneous | To make 100 | To make 100 | To make 100 | To make 100 | To make 100 |

|  | Formula 11b | Formula 12b | Formula 13b | Formula 14b | Formula 15b |
| --- | --- | --- | --- | --- | --- |
| Vinylpyrrolidone homopolymer (a): Luviskol ® K 90 - 20% (expressed as solids content) | 0.05 to 3.0 | 0.1 to 2.5 | 0.2 to 2.0 | 0.5 to 1.5 | 0.8 to 1.2 |
| Copolymer (b): BALANCE ® RCF (expressed as solids content) | 0.01 to 5.0 | 0.15 to 4.0 | 0.1 to 2.0 | 0.5 to 1.5 | 0.2 to 0.7 |

-continued

| | Formula 11b | Formula 12b | Formula 13b | Formula 14b | Formula 15b |
|---|---|---|---|---|---|
| Carbomer | 0.02 to 3.0 | 0.05 to 2.0 | 0.05 to 1.5 | 0.2 to 1.0 | 0.35 to 0.8 |
| Miscellaneous | To make 100 | To make 100 | To make 100 | To make 100 | To make 100 |

As contemplated herein, "Miscellaneous" is understood to mean a cosmetic carrier, in particular water and optionally further customary components of styling products.

Examples

1. The following styling gel was prepared:

| Composition 1 | | | |
|---|---|---|---|
| Component/ raw material | % by weight | INCI name | Manufacturer |
| Water, demineralized, without H$_2$O$_2$ | 93.320 | | |
| Carbomer 20,000-30,000 mPas (0.2%) | 0.505 | Carbomer | |
| Luviskol ® K90 - 20% | 5.000 | Acrylates/ Hydroxyesters Acrylates Copolymer | BASF |
| BALANCE ® RCF | 1.665 | Acrylates Copolymer (and) Water | AkzoNobel |
| AMP Ultra ® PC 2000 | 0.510 | PEG-40 Hydrogenated Castor Oil | Dow Chemical |
| Total | 100 | | |

In the table, quantities are expressed in % by weight of the particular raw material, based on the overall composition.

Stiffness:

850 mg of a test composition in gel form was rubbed into a dry hair strand with the fingers (Euro-Naturhaar 826500 from Kerling, compacted glued tress, adhesively bonded on one side, total length 150 mm, free length 130 mm, width 20 mm, weight 1.8±0.2 g). The hair strand treated with the test composition to be examined was straightened in a Teflon bar having a diameter of 20 mm. The prepared strands were subsequently dried and conditioned overnight in a climatic chamber at 21° C. and 50% relative humidity.

The conditioned strand was carefully removed from the Teflon bar. The resulting flat strand was placed on measuring blocks spaced 40 mm apart. The 3PB adapter of an AMETEK LF Plus universal test apparatus from AMETEK Precision Instruments Europe GmbH, Lloyd product group, was mounted centrally above the strand. The entire measurement was performed in the climatic chamber under constant climatic conditions at 21° C. and 50% relative humidity.

To create standardized starting conditions, the measurement began with an initial load of 0.05 N upon start-up. The strand was subsequently compressed by 15 mm at a speed of 500 mm min-1, the required force for this being measured. After the characteristic force K at the maximum deformation of 15 mm was recorded.

By use of this measuring method, the stiffness of the polymer film, based on the force Fmax as a parameter, and the degree of hold of the hairstyle hold thus produced may be measured.

Ten strands were created and measured for each test composition. Stiffness values in the range of 3-8 N were obtained (arithmetic mean).

Long-Term Hold:

The composition was tested with regard to its shaping properties by employing a long-lasting hold measurement. Standardized hair strands from Kerling (Article No. 826500) of hair type European Natural, color 6/0), having a length (Lmax) of 220 mm and a weight of 3.0 g, were used for this purpose. The strands were prepared by washing with a 12.5% by weight sodium laureth sulfate solution. The hair strands were dried overnight at 318 K in a drying oven.

The hair was soaked in lukewarm water for 20 min and then blotted until approximately 50% residual moisture remained in the hair.

750 mg of the composition was applied to each of the hair strands and rubbed in. The hair strands were placed in a Teflon bar, straightened using a steel roller, and dried overnight at 21° C. and 50% relative humidity.

The hair strands were subsequently clamped at one end into a holding apparatus and stored for a period of six hours at 21° C. and 85% relative humidity. The strand length protruding from the holding apparatus before (Lo) and after (Lt) the storage was measured for calculating the long-lasting hold (LLH).

The long-lasting hold is a measure of the change over time in the length of a hair strand that is fixed by employing a hair shaping agent. The higher the LLH value, the less the change in length of the hair strand under the effect of humidity in a given time period, and the better the degree of hold of the hair shaping agent.

The long-lasting hold was calculated according to the following formula:

$$LLH = 1 - (L_t - L_o / L_{max})$$

An LLH value of 40-60% was determined (arithmetic mean of the LLH values from 10 test strands).

The gel as contemplated herein thus showed an exceptionally good combination of long-term hold and stiffness.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition for temporarily shaping keratinic fibers, comprising:
   a vinylpyrrolidone homopolymer, wherein the vinylpyrrolidone homopolymer has an intrinsic viscosity (K)

value of from about 90.0c to about 98.0c (at 1% m/V in water), and wherein the vinylpyrrolidone homopolymer is present in the cosmetic composition at a concentration of about 1 weight percent, based on a total weight of the cosmetic composition; and a crosslinked acrylate copolymer present in the cosmetic composition at a concentration of about 0.5 weight percent, based on the total weight of the cosmetic composition, and wherein the crosslinked acrylate copolymer comprises at least one of the following structural units (b-1) and (b-2),

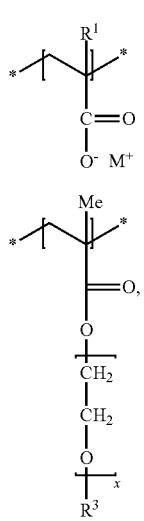

where
$R^1$ stands for a hydrogen atom or a methyl group,
$R^3$ stands for a ($C_8$-$C_{30}$) alkyl group,
$M^+$ stands for a physiologically acceptable cation, and
$x$ stands for an integer from 5 to 35, and wherein the crosslinked acrylate copolymer has the INCI name Acrylates/Ceteareth-20 Methacrylate Crosspolymer.

2. The cosmetic composition according to claim 1, wherein the vinylpyrrolidone homopolymer has a K value in water of about 90c (1% by weight solution of PVP, Brookfield, at 23° C.).

3. The cosmetic composition according to claim 2, wherein the cosmetic composition further comprises aminomethyl propanol.

4. The cosmetic composition according to claim 1, wherein the composition also comprises at least one thickener, wherein the thickener comprises a a synthetic high molecular weight polymer of acrylic acid.

5. The cosmetic composition according to claim 4, which, based on the total weight of the cosmetic composition, comprises:
about 0.05 to about 1.5% by weight of the thickener.

6. The cosmetic composition according to claim 1, wherein the composition is present as a hair gel, hair spray, hair wax, or hair foam.

7. The cosmetic composition according to claim 1, wherein the acrylate copolymer comprises the first structural unit (b-1) and the second structural unit (b-2) wherein $R^3$ is a combination of linear C16 and C18 alkyl groups.

8. The cosmetic composition according claim 1, wherein the acrylate copolymer comprises the structural unit (b-1) and the structural unit (b-2).

9. The cosmetic composition according to claim 1, which, based on the total weight of the cosmetic composition, comprises:
a thickener at from about 0.2 to about 0.8% by weight.

10. A method for temporarily shaping keratinic fibers, comprising:
providing a cosmetic composition comprising:
a vinylpyrrolidone homopolymer, wherein the vinylpyrrolidone homopolymer has an intrinsic viscosity (K) value of from about 90.0c to about 98.0c (at 1% m/V in water), and wherein the vinylpyrrolidone homopolymer is present in the cosmetic composition at a concentration of about 1 weight percent, based on a total weight of the cosmetic composition; and
a crosslinked acrylate copolymer present in the cosmetic composition at a concentration of about 0.5 weight percent, based on the total weight of the cosmetic composition, and wherein the crosslinked acrylate copolymer comprises at least one of the following structural units (b-1) and (b-2),

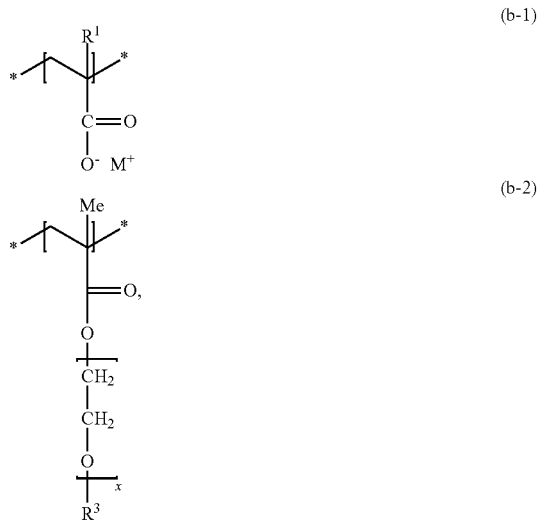

where
$R^1$ stands for a hydrogen atom or a methyl group,
$R^3$ stands for a ($C_8$-$C_{30}$) alkyl group,
$M^+$ stands for a physiologically acceptable cation, and
$x$ stands for an integer from 5 to 35, wherein the crosslinked acrylate copolymer has the INCI name Acrylates/Ceteareth-20 Methacrylate Crosspolymer; and
applying the cosmetic composition to keratinic fiber.

11. The method according to claim 10, wherein providing the cosmetic composition comprises providing the cosmetic composition wherein the vinylpyrrolidone homopolymer has a K value of about 90c.

12. The method according to claim 10, wherein the keratinic fibers are human hair.

* * * * *